(12) United States Patent
Watson, Jr. et al.

(10) Patent No.: US 6,740,095 B2
(45) Date of Patent: *May 25, 2004

(54) UMBILICAL CORD CLAMP AND CUTTER

(75) Inventors: Richard L. Watson, Jr., McPherson, KS (US); Ronald B. Hicks, San Antonio, TX (US); Carrie D. M. Bader, Austin, TX (US); Philip Y. C. Leung, Austin, TX (US)

(73) Assignee: Maternus Partners, Ltd., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/232,029

(22) Filed: Aug. 30, 2002

(65) Prior Publication Data

US 2002/0198535 A1 Dec. 26, 2002

Related U.S. Application Data

(63) Continuation of application No. 09/874,770, filed on Jun. 5, 2001, now Pat. No. 6,443,958.

(51) Int. Cl.[7] ........................ A61B 17/42; A61B 17/46; A61D 1/10
(52) U.S. Cl. ........................ 606/120; 606/170; 606/244
(58) Field of Search ........................ 606/1, 120, 151, 606/157, 205, 174, 142, 167; 128/346, 325

(56) References Cited

U.S. PATENT DOCUMENTS

| | | | | |
|---|---|---|---|---|
| 1,983,969 A | * | 12/1934 | Davis | 131/246 |
| 4,112,944 A | * | 9/1978 | Williams | 604/244 |
| 4,212,303 A | | 7/1980 | Nolan | 128/346 |
| 4,781,188 A | | 11/1988 | Collins | 128/305 |
| 4,856,517 A | | 8/1989 | Collins et al. | 128/346 |
| 5,009,657 A | | 4/1991 | Cotey et al. | 606/120 |
| 5,254,129 A | * | 10/1993 | Alexander | 606/170 |
| 5,415,665 A | | 5/1995 | Hessel et al. | 606/120 |
| 5,462,555 A | | 10/1995 | Bolanos et al. | 606/120 |
| 5,520,699 A | * | 5/1996 | Hessel et al. | 606/120 |
| 5,575,796 A | | 11/1996 | King et al. | 606/120 |
| 5,584,840 A | | 12/1996 | Ramsey et al. | 606/120 |
| 5,608,382 A | | 3/1997 | Webb et al. | 340/573 |
| 5,667,516 A | | 9/1997 | Allen | 606/120 |
| 5,676,672 A | | 10/1997 | Watson et al. | 606/120 |

(List continued on next page.)

OTHER PUBLICATIONS

Umbilicutter, Pregnancy Institute web site, http://www.preginst.com/umbilical_cord_clamp_cut.htm, and http://www.pregnist.com/plans.htm, drawing dated Jan. 26, 1990, publication date unknown.

*Primary Examiner*—John J. Calvert
*Assistant Examiner*—Robert H. Muromoto
(74) *Attorney, Agent, or Firm*—Loeffler Jonas & Tuggey LLP

(57) ABSTRACT

A novel umbilical cord clamp and a combined umbilical cord clamp and cutter are provided for clamping and cutting umbilical cords in one motion. The cutter comprises two shells joined by a longitudinal hinge. A transverse blade is mounted in one shell, and a cutting support is mounted in the other shell across from the blade. A clamping member is provided on one side of the blade as part of the cutter, and a removable clamp is provided on the other side of the blade. The umbilical cord to be cut is oriented generally parallel to the hinge and lying across the cutting support. As the shells of the cutter are closed, the umbilical cord is clamped on both sides of the blade, and the blade severs the umbilical cord in the same motion. After the cut is completed, the removable clamp is removed from the cutter, preferably revealing an aesthetically pleasing form such as the face of a koala bear.

16 Claims, 18 Drawing Sheets

U.S. PATENT DOCUMENTS

| | | |
|---|---|---|
| 5,697,938 A | 12/1997 | Jensen et al. ............... 606/120 |
| 5,797,922 A | 8/1998 | Hessel et al. ................. 60/120 |
| 5,817,103 A | 10/1998 | Bell ........................... 606/120 |
| 5,860,989 A | 1/1999 | Webb ......................... 606/120 |
| 5,913,862 A * | 6/1999 | Ramsey et al. ............. 606/120 |
| 5,921,991 A | 7/1999 | Whitehead et al. ......... 606/120 |
| 5,925,052 A * | 7/1999 | Simmons .................... 606/120 |
| 5,947,980 A | 9/1999 | Jensen et al. ............... 606/120 |
| 5,968,054 A | 10/1999 | Yeatts, II et al. ........... 606/120 |
| 5,997,548 A | 12/1999 | Jahanger .................... 606/120 |
| 6,059,794 A | 5/2000 | Webb ......................... 606/120 |
| 6,144,304 A | 11/2000 | Webb ....................... 340/573.4 |

* cited by examiner

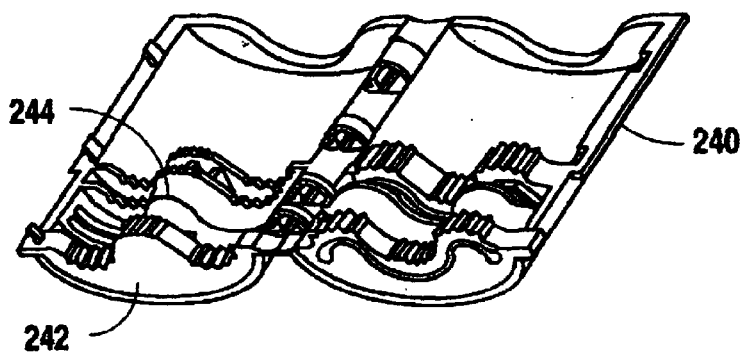
Fig. 31
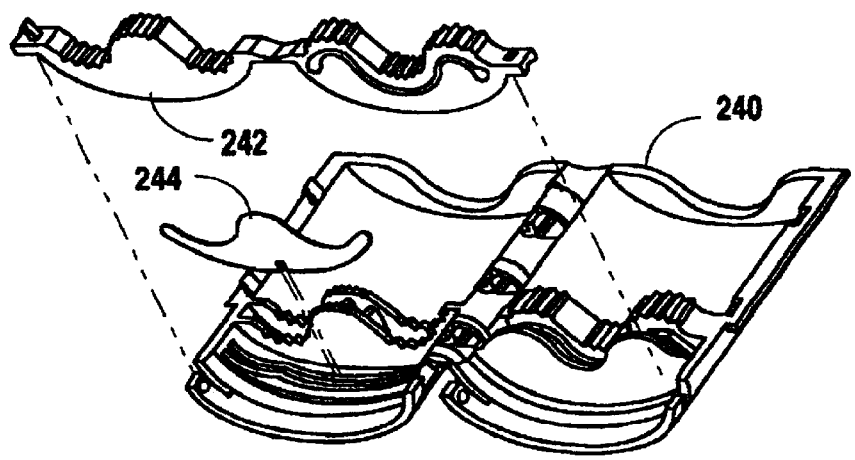
Fig. 32
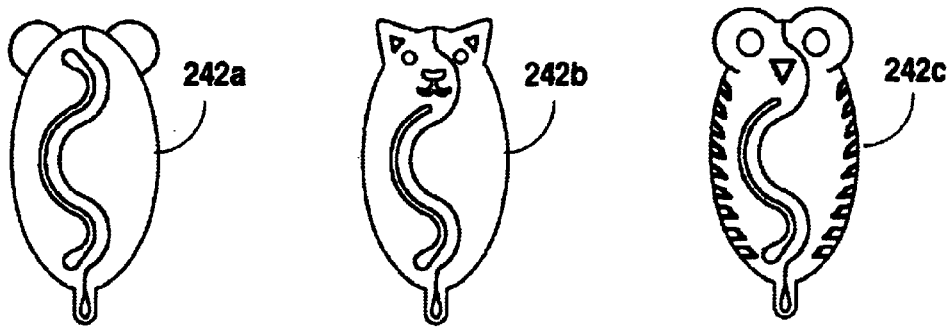
Fig. 33  Fig. 34  Fig. 35

UMBILICAL CORD CLAMP AND CUTTER

This is continuation of application Ser. No. 09/874,770, filed Jun. 5, 2001, now U.S. Pat. No. 6,443,958.

BACKGROUND OF THE INVENTION

1. Field of the Invention

This invention relates generally to umbilical cord clamps and cutters, and more particularly to a combined umbilical cord clamp and cutter for clamping and cutting an umbilical cord in one continuous motion.

2. Description of the Related Art

A number of clamps and cutters are known in the art for clamping and cutting the umbilical cords of newborn babies. Perhaps the most common clamp currently used for such purposes is the umbilical cord clamp disclosed in U.S. Pat. No. 4,212,303, issued to Nolan on Jul. 15, 1980 and assigned to Hollister Incorporated ("the Hollister clamp"). The Hollister clamp comprises a pair of flexible arms joined by an integral hinge to form a generally V-shaped clamp. The interior of each arm has serrations or ridges for grasping the umbilical cord. The free end of one of the arms has a flexible tongue that cooperates with a recess on the free end of the other arm to close the clamp about the umbilical cord. In practice, two Hollister clamps are clamped to the umbilical cord in spaced relation to one another, and the cord is then cut between the two clamps using scissors or a scalpel. One clamp is temporarily left on the baby's navel, and the other clamp is disposed of with the placenta. The Hollister clamp has several drawbacks. First, it takes three separate instruments (two clamps and a cutting tool) to accomplish the process of cutting the umbilical cord using the Hollister clamp. In an alternative practice, one Hollister clamp is frequently used in conjunction with a hemostat, and the cord is cut between the Hollister clamp and the hemostat. If a hemostat is used instead of a second Hollister clamp during the cutting process, the overall procedure is even more cumbersome because the hemostat is typically replaced with a second Hollister clamp after the cord is cut, which adds a fourth instrument. Second, the Hollister clamp does not provide any shield from the splatter of blood when the umbilical cord is cut, which presents a danger of blood-borne pathogens to hospital personnel. Additionally, the Hollister clamp is not aesthetically attractive when left on the baby's navel.

Several combined clamp and cutter devices have been developed that essentially employ the Hollister clamp. An example of one such device is shown in U.S. Pat. No. 5,925,052, issued to Simmons on Jul. 20, 1999 ("Simmons"). Simmons discloses a scissor-type device with a cutting blade that receives an assembly comprising a pair of Hollister-type clamps. As the scissors are squeezed together, the blade severs the umbilical cord and the clamp assembly while closing the two clamps on either side of the cut. Although the Simmons device combines the two clamps and cutter into a single tool, it does not solve the problem of the need for a shield to guard against the splatter of blood nor the problem of poor aesthetics. A similar device is also disclosed in U.S. Pat. No. 5,968,054, issued to Yeatts et al. on Oct. 19, 1999, which suffers from the same disadvantages.

U.S. Pat. No. 5,697,938, issued to Jensen et al. on Dec. 16, 1997 ("Jensen"), discloses a disposable device for squeezing and cutting an umbilical cord comprising a pair of clamps that mate with a sliding unit which contains a blade. As the sliding unit closes the clamps, the blade severs the umbilical cord. Again, however, the Jensen device does not have a shield to prevent the splatter of blood, and the clamps are modifications of the Hollister clamp which are not aesthetically appealing.

U.S. Pat. No. 5,676,672, issued to Watson et al. on Oct. 14, 1997 ("Watson"), addressed the problem of the splatter of blood by housing a cutting blade and a circular clamping surface inside a cooperating pair of semi-cylinders joined by a hinge. A similar pair of semi-cylinders with a second circular clamping surface is connected to the first pair of semi-cylinders with a breakable joint. As the two pair of semi-cylinders are closed in clamshell fashion, the clamping surfaces compress the umbilical cord. Thereafter, the blade is depressed to sever the cord, and the semi-cylinders prevent the blood from splattering. Then, the two pair of semi-cylinders are separated by breaking the breakable joint. The pair of semicylinders without the blade is left with the baby, and the other pair is discarded with the placenta. Although the Watson device solved the blood splatter problem, the pair of semi-cylinders left with the baby is bulky and aesthetically unattractive. Additionally, although the Watson device was intended to enable one-handed operation, the Watson device presents significant difficulties in the process of depressing the blade and breaking the clamps apart.

Thus, a need exists for a disposable umbilical cord clamp and cutter that prevents the splatter of blood, is easy to operate with one hand, and leaves an aesthetically pleasing clamp on the baby's navel

SUMMARY OF THE INVENTION

To solve the problems mentioned above, a cutter device in accordance with the present invention comprises a pair of shells connected by a longitudinal hinge. The first shell has a transverse blade fixedly mounted therein and a clamping member adjacent the blade on the "mother" side of the blade. The second shell has a cutting support aligned with the blade. The cutter is positioned with the umbilical cord lying across the cutting support, which preferably comprises a pair of walls separated by a gap into which the blade may pass. On the "baby" end of the cutter, a removable clamp is inserted between the shells. The removable clamp has a clamp body with a corrugated clamping surface, a strap for cooperating with the clamping surface, and a hinge joining the strap to the clamp body. The clamp body has a crown opposite the clamping surface for engagement with the interior surface of the first shell, and the exterior surface of the strap engages the interior surface of the second shell. Thus, as the two shells are closed, the clamping member in the first shell of the cutter compresses the umbilical cord on the "mother" side of the blade, the clamping surface of the removable clamp compresses the umbilical cord against the strap of the removable clamp on the "baby" side of the blade, and the blade severs the umbilical cord, all in one motion through the action of one hand of the user.

As the umbilical cord is severed as described above, the shells substantially surround the cord and thereby prevent the splattering of blood. Preferably, the clamping member in the first shell has at least one tab for engagement with a catch extending from the second shell. More preferably, two tabs are provided for engagement with the catch. Together, the tabs and catch constitute a latch to keep the shells closed after the cut is complete. Toward the end of the closing of the shells, the first tab clicks into engagement with the catch to indicate that the shells are prevented from reopening. Upon further squeezing of the shells, the second tab clicks into engagement with the catch to indicate that the cut is complete. Also, each shell is preferably provided with a guide that engages the guide of the other shell to form a detent that holds the shells in a partially open initial position before the cutting process is begun. The exterior of each shell is preferably provided with a plurality of protrusions or recesses to assist the user in gripping the cutter. Together, the shells have an overall outer shape that comfortably fits in the palm of the user's hand.

In the vicinity where the removable clamp is mounted to the shells of the cutter, the periphery of each shell is provided with an indentation to allow access to a protrusion of the removable clamp. After the umbilical cord is severed, the user may use a thumb to apply a force to the protrusion of the removable clamp in order to dislodge the removable clamp from the shells. The removable clamp is then left with the baby, and the cutter is discarded with the placenta. The removable clamp is preferably shaped like the head of a koala bear, with facial indicia (e.g., eyes, nose, and mouth) on the face. When the removable clamp is engaged with the shells of the cutter, the face of the koala bear is toward the interior of the cutter. After the removable clamp is removed from the cutter, the baby is left with a clamp on its navel that resembles a koala bear, which is much more attractive than a Hollister clamp. Therefore, the removable clamp of the present invention is aesthetically pleasing as well as very practical. The removable clamp may also be made in the shape of various other animals, such as a teddy bear or duck, or other non-animal shapes, such as an ellipse.

In addition, the removable clamp is preferably provided with a recess on the back side of the clamp body. The recess provides for reduced weight of the clamp and tends to eliminate sink marks if the clamp is manufactured by a molding process. Also, the recess allows for a wireless transmitter to be inserted in the clamp so that the baby can be tracked electronically.

It is an object of the present invention to provide a combined umbilical cord clamp and cutter for clamping and cutting an umbilical cord in one motion.

It is a further object of the present invention to provide a disposable umbilical cord clamp and cutter that prevents the splatter of blood or other fluids when cutting an umbilical cord.

It is another object of this invention to provide a combined umbilical cord clamp and cutter that is easily and safely operable with one hand.

It is still another object of this invention to provide an improved umbilical cord clamp that is aesthetically pleasing.

Further objects and advantages of the present invention will be readily apparent to those skilled in the art from the following detailed description taken in conjunction with the annexed sheets of drawings, which illustrate a preferred embodiment of the invention.

BRIEF DESCRIPTION OF THE DRAWINGS

FIG. 31 is a perspective view of still another alternative umbilical cord cutter and clamp in accordance with the present invention.

FIG. 32 is an exploded perspective view of the umbilical cord cutter and clamp of FIG. 31.

FIG. 33 is a front elevational view of one embodiment of the clamp of FIG. 31.

FIG. 34 is a front elevational view of another embodiment of the clamp of FIG. 31.

FIG. 35 is a front elevational view of yet another embodiment of the clamp of FIG. 31.

DETAILED DESCRIPTION OF A PREFERRED EMBODIMENT

Figure 1:
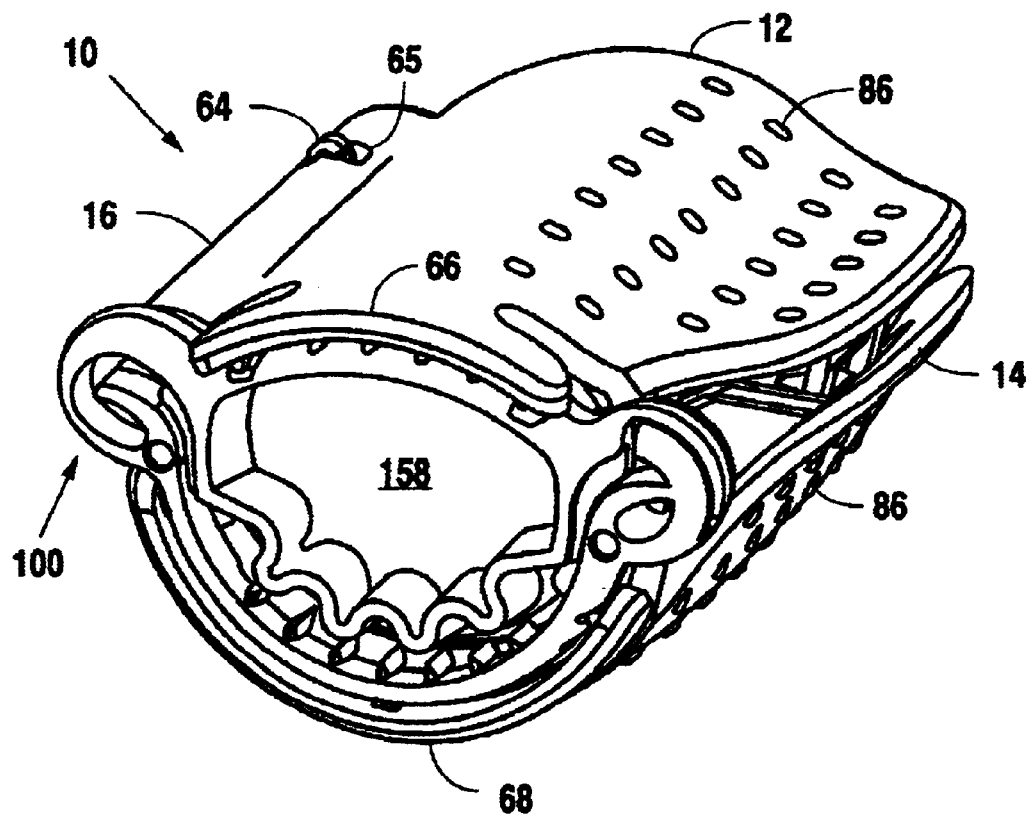
FIG. 1 is a perspective view of an umbilical cord cutter and removable clamp in accordance with the present invention shown in a closed position.
Figure 2:
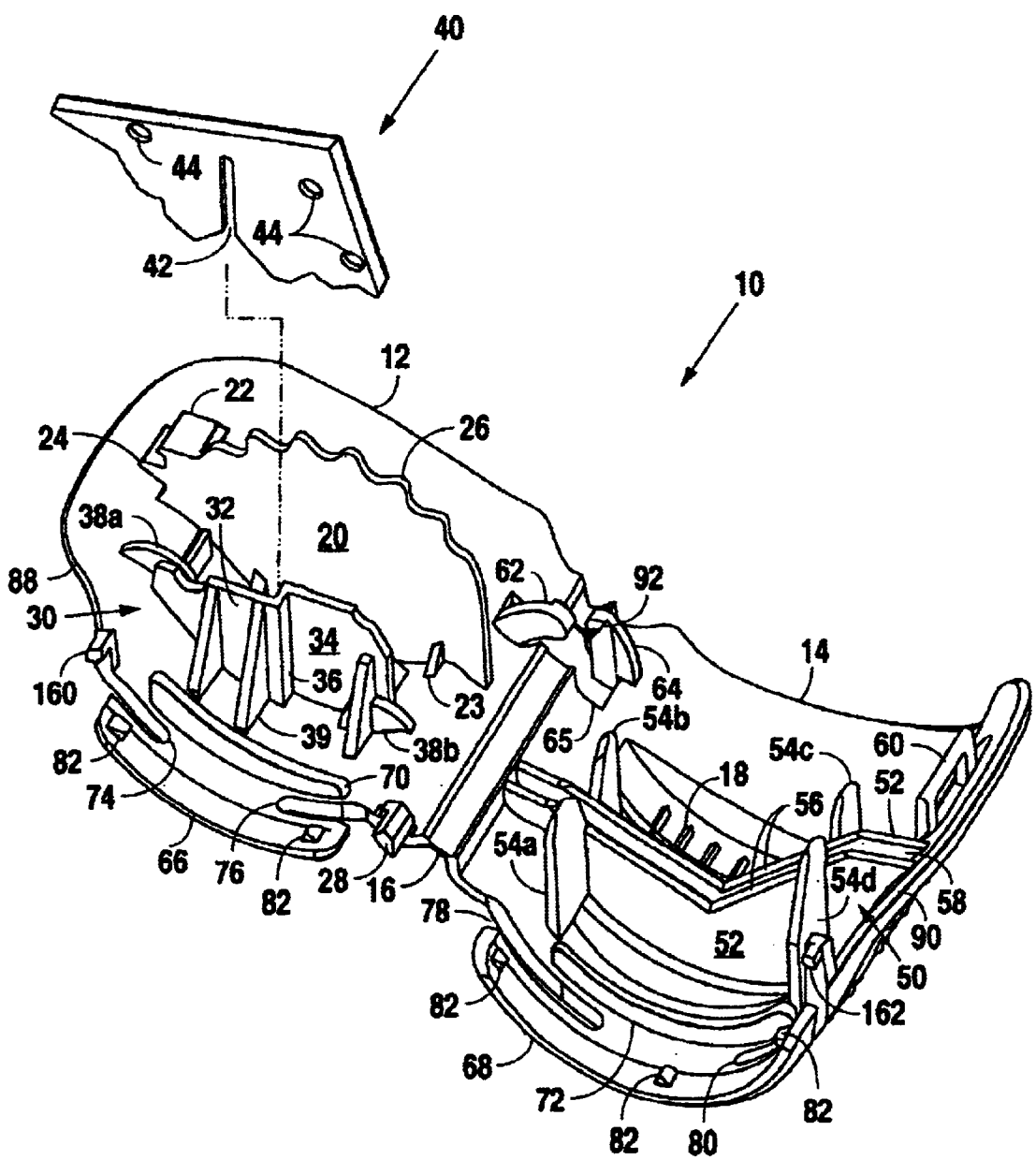
FIG. 2 is an exploded perspective view of the umbilical cord cutter of FIG. 1 shown in an open position.
Figure 3:
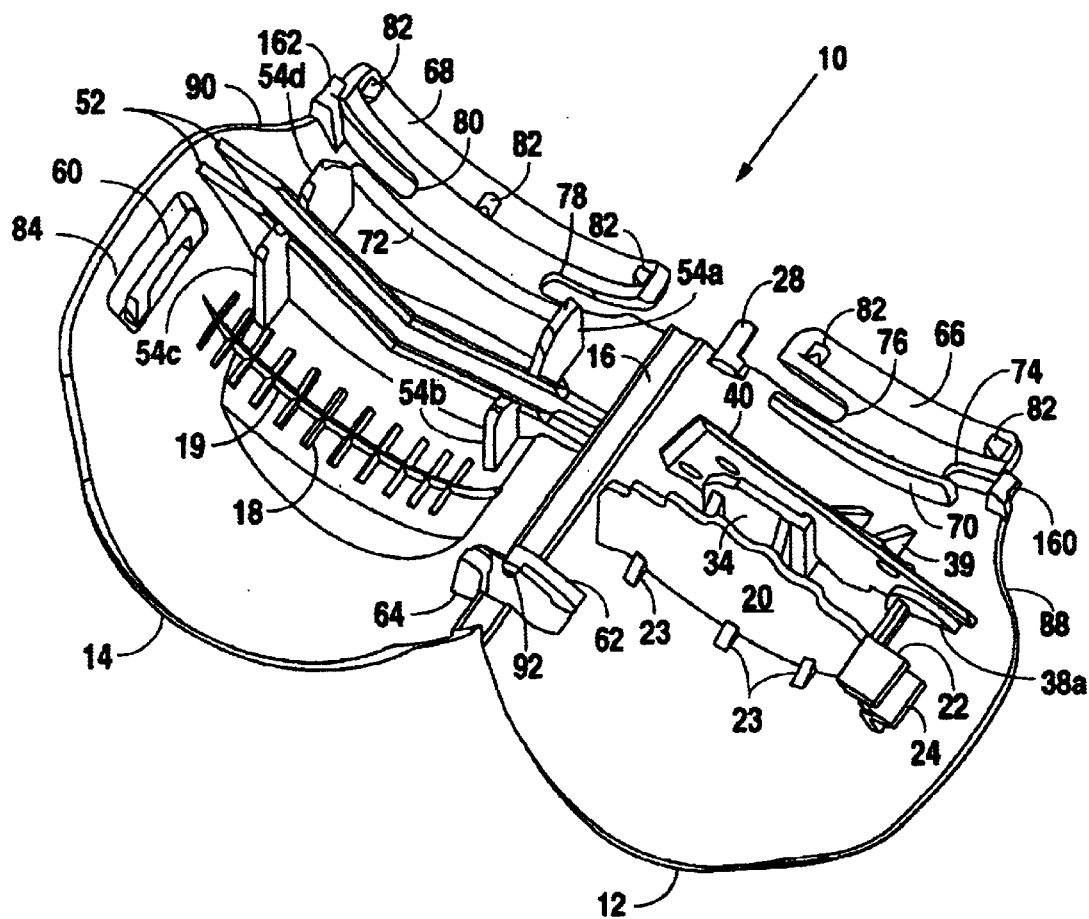
FIG. 3 is another perspective view of the umbilical cord cutter of FIG. 1 shown in an open position.

Referring primarily to FIGS. 1–6, a cutter 10 in accordance with the present invention comprises a first shell 12 joined to a second shell 14 by a longitudinal hinge 16. Preferably, hinge 16 is integral with shells 12 and 14, but shells 12 and 14 could be made separately and joined with a separate hinge. As discussed further below, a removable baby clamp 100 is installed on one end of cutter 10. Baby clamp 100 is not shown in FIGS. 2, 3, and 6 for the sake of clarity. A blade 40 is transversely mounted to the inside of shell 12 with a blade holder 30, which extends from the inner surface of shell 12 Blade 40, which is preferably made of surgical steel about 0.03 in. thick, is not shown in FIGS. 4 and 5 for the sake of clarity. The end of cutter 10 to which baby clamp 100 is mounted is referred to as the "baby end," and the other end is referred to as the "mother end." As best seen in FIG. 2, blade holder 30 preferably comprises two upstanding walls 32 and 34 connected by a support member 36. Additional support members 38a and 38b are provided to stabilize the inner and outer ends of blade 40, and a plurality of gussets 39 are provided to further strengthen and stiffen blade holder 30. Blade 40 contains a slot 42 such that blade 40 straddles support member 36. Tooling holes 44 are provided to facilitate the installation of blade 40 by pressing it into blade holder 30.

On the inside of shell 14 opposite blade 40, a cutting support 50 is provided to support an umbilical cord (not shown) while the cord is being cut by blade 40. Cutting support 50 preferably comprises a pair of upstanding walls 52 separated by a gap 58 into which blade 40 protrudes as the cord is being cut. The width dg of gap 58 (best shown in FIG. 8) is preferably about 0.06 in. If width dg is too wide (for example, greater than about 0.125 in.), blade 40 will tend to press the umbilical cord into gap 58 rather than cut through the umbilical cord. Walls 52 preferably have relatively sharp upper edges 56 to help prevent longitudinal movement of the umbilical cord during the cutting process. Buttresses 54a–d may be provided to strengthen and stiffen walls 52 and to serve as lateral constraints to help prevent excessive lateral movement of the umbilical cord. The "V" shape of walls 52 also helps to keep the umbilical cord properly positioned for cutting.

On the mother side of blade 40, a clamping member 20 extends transversely from shell 12. Preferably, clamping member 20 has a plurality of teeth 26 for engaging the umbilical cord, and clamping member 20 preferably cooperates with a plurality of ridges 18 formed on the inside of shell 14 opposite clamping member 20. Ridges 18 may be connected by a central ridge 19. Clamping member 20 is preferably stabilized by a plurality of gussets 23.

To keep cutter 10 closed after the umbilical cord has been severed, a pair of tabs 22, 24 is provided on clamping member 20 for cooperation with a catch 60 that depends from shell 14. As the cut is being performed, first tab 22 will click into engagement with catch 60, which prevents shells 12 and 14 from accidentally coming open. Thereafter, upon further squeezing of shells 12 and 14, tab 24 will click into engagement with catch 60 to indicate that the cut has been completed. In addition to providing a locking function, the clicking of tabs 22 and 24 into engagement with catch 60 provides audible and tactile indications to the user that shells 12 and 14 are restricted from reopening and that the cut has been completed. An opening 84 is preferably created in shell 14 by a protrusion of the mold used to form catch 60. If for some reason cutter 10 needs to be opened after the umbilical cord has been severed, opening 84 provides access to the interior of cutter 10 so that catch 60 may be deflected outward and thereby disengaged from tabs 22 and 24. Alternatively, catch 60 may be accessed for such purpose through the opening between shells 12 and 14 at the mother end of cutter 10. A plurality of bumps 86, or alternatively depressions, may be provided on shells 12 and 14 to facilitate grasping by the user.

Figure 14:
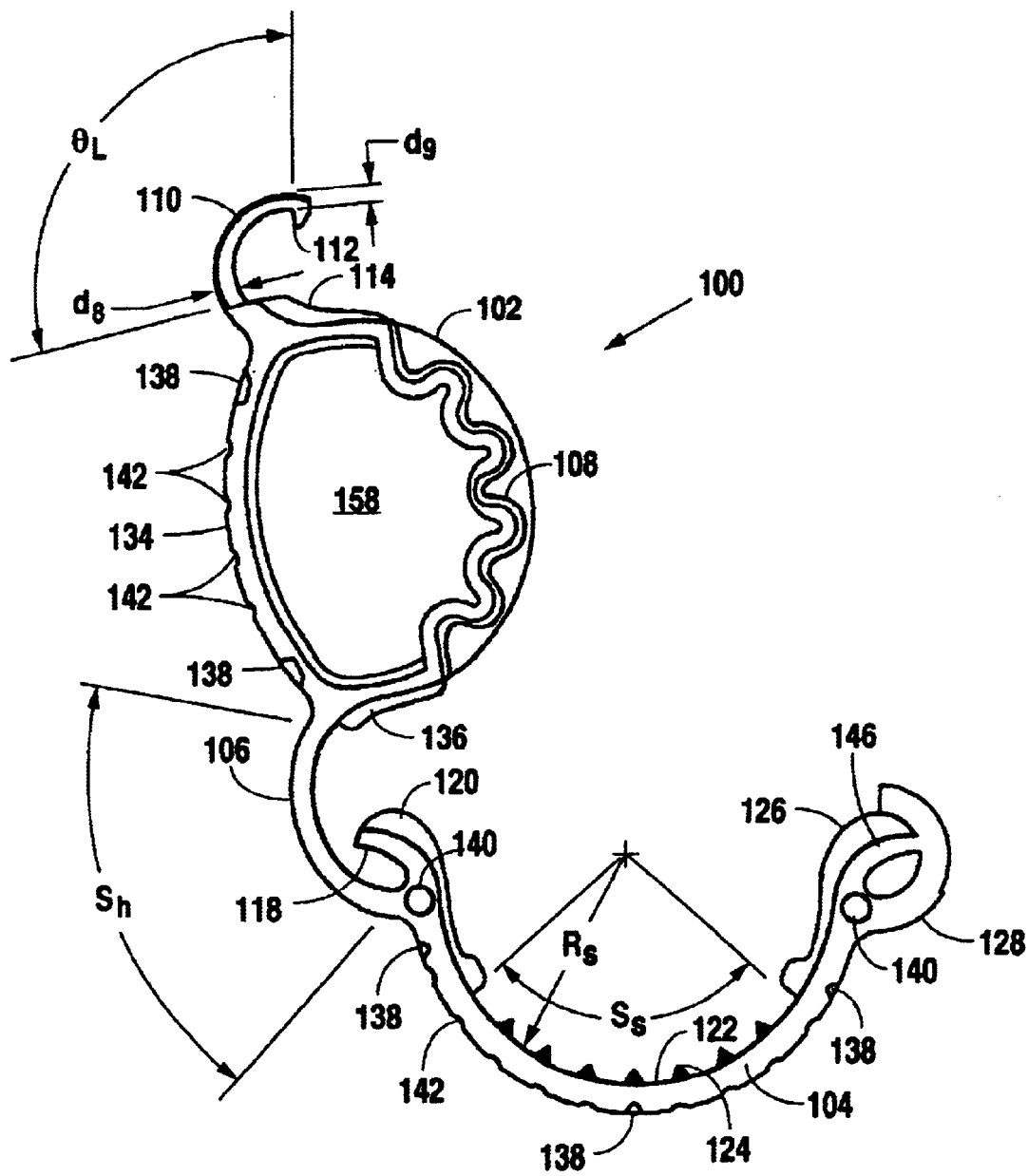
FIG. 14 is a front elevational view of the removable clamp of FIG. 1 shown in an open position.
Figure 15:
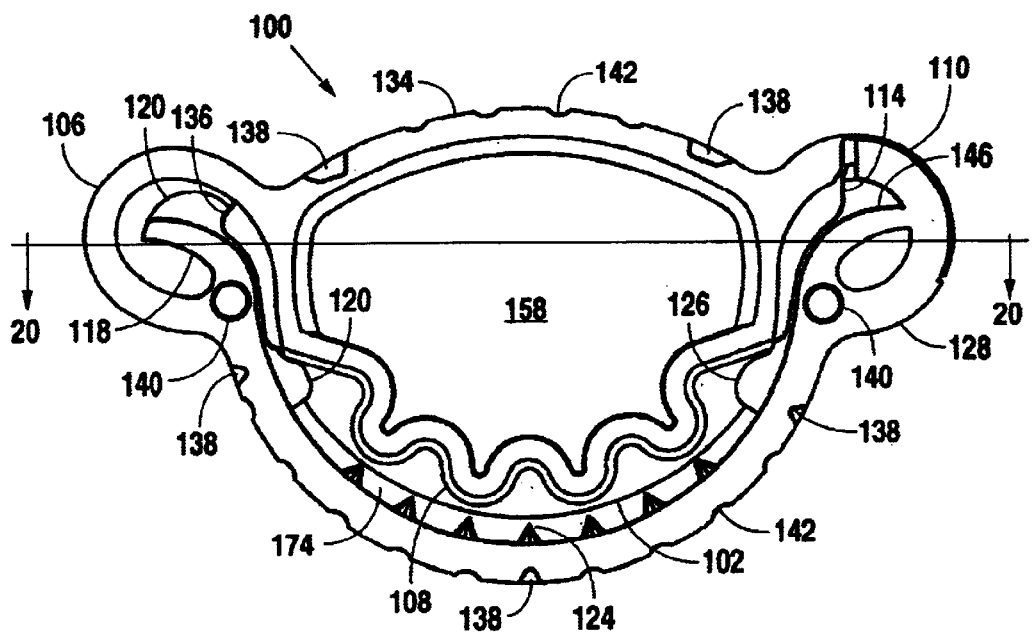
FIG. 15 is a front elevational view of the removable clamp of FIG. 1 shown in a closed position.
Figure 16:
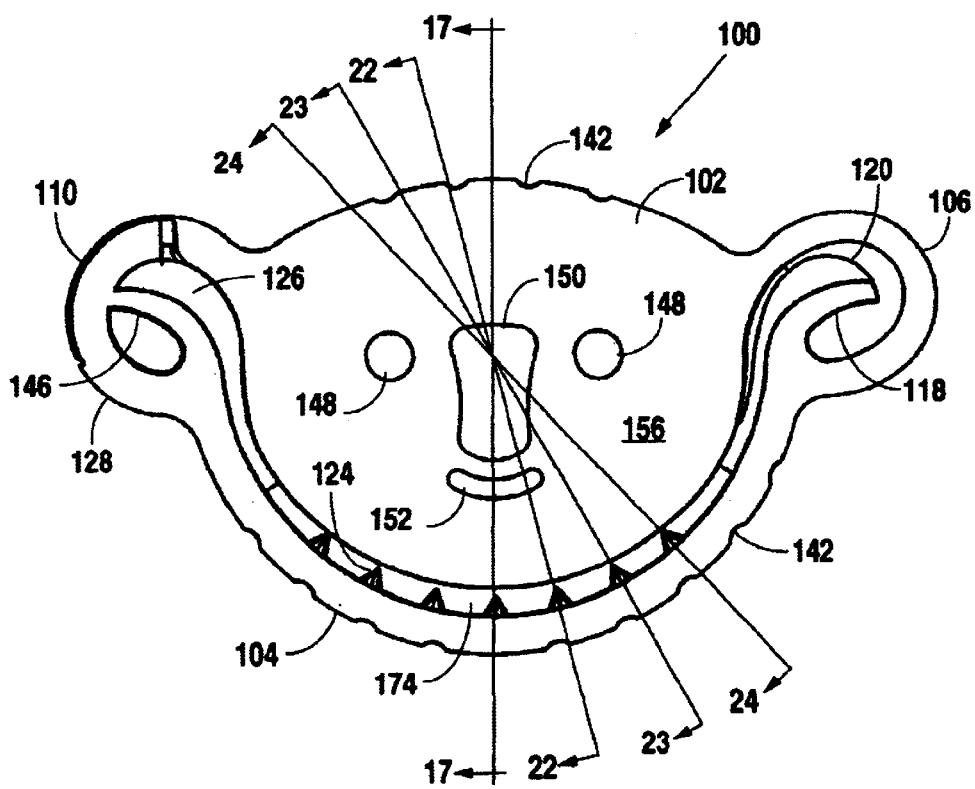
FIG. 16 is a rear elevational view of the removable clamp of FIG. 1 shown in a closed position.

To facilitate installation and removal of baby clamp 100 to and from cutter 10, slots 74 and 76 are provided on the baby end of shell 12 to form a flexible shelf 66, and slots 78 and 80 are provided on the baby end of shell 14 to form a flexible shelf 68. A plurality of nibs 82 are provided on shelves 66 and 68 for cooperation with recesses 138 on baby clamp 100, as best shown in FIG. 14, to retain baby clamp 100 on cutter 10. Guides 28, 160, and 162 also help to properly position baby clamp 100 with respect to cutter 10. Shells 12 and 14 and baby clamp 100 are preferably sized such that shelves 66 and 68 exert a slight compressive force on baby clamp 100 when cutter 10 is in a closed position. Short fences 70 and 72 are preferably provided just inside shelves 66 and 68, respectively, to prevent baby clamp 100 from sliding too far into the interior of cutter 10. Indentations 88 and 90 are provided in shells 12 and 14, respectively, to facilitate removal of baby clamp 100 after the umbilical cord has been cut by allowing the user to place a thumb behind an ear 128 of baby clamp 100 and dislodge baby clamp 100 from cutter 10.

Figure 4:
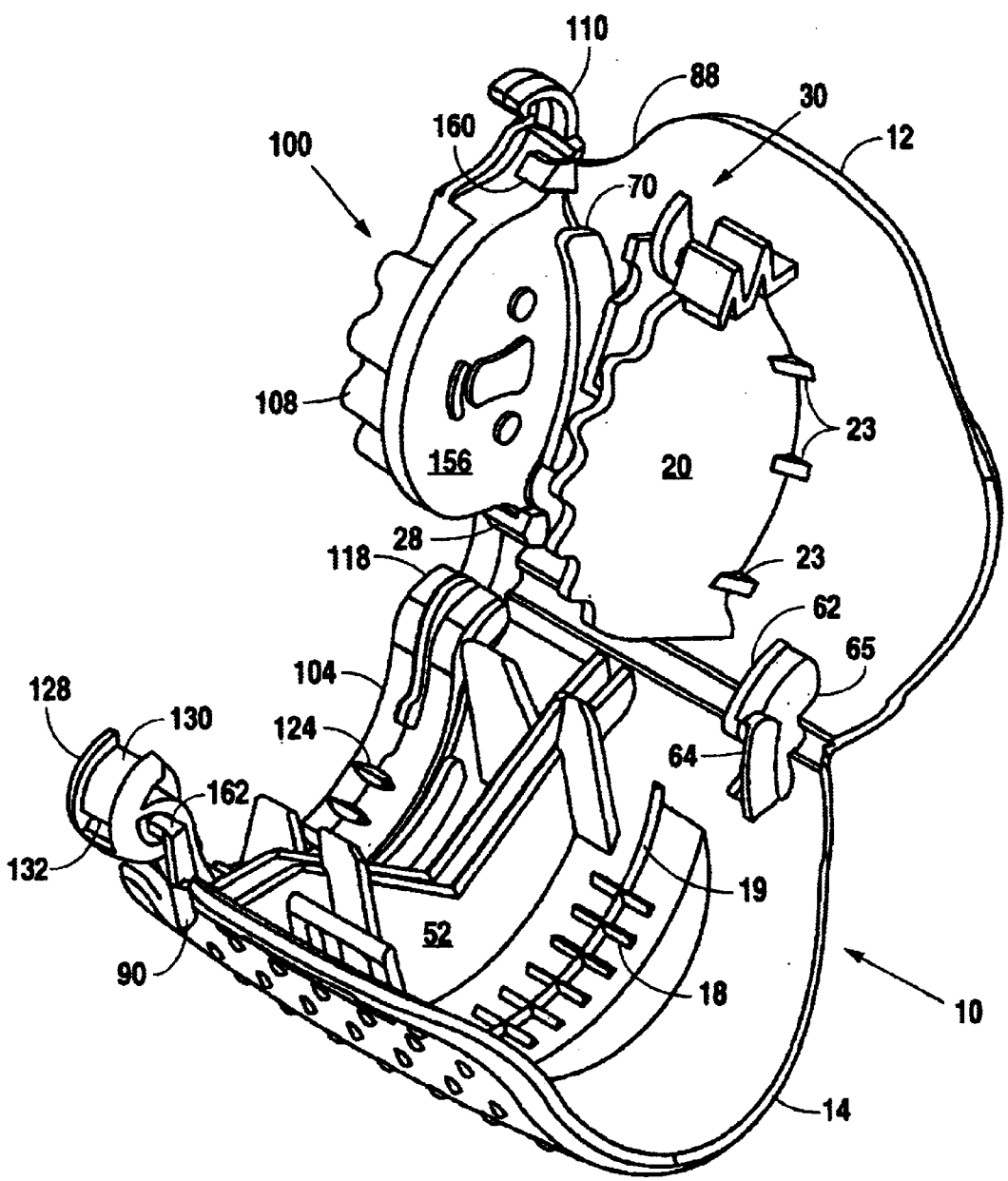
FIG. 4 is yet another perspective view of the umbilical cord cutter and removable clamp of FIG. 1 shown in an open position without the blade.
Figure 5:
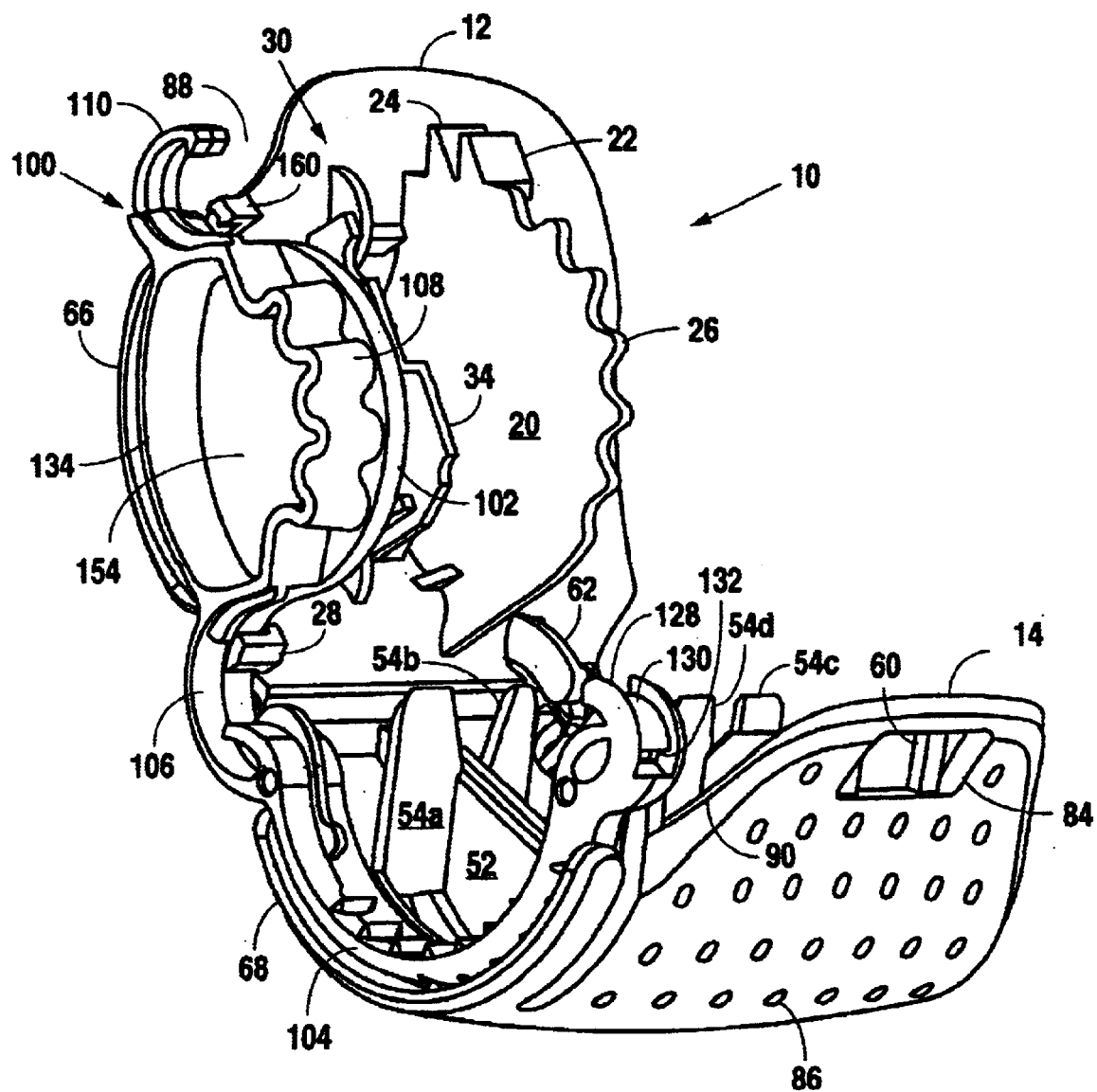
FIG. 5 is still another perspective view of the umbilical cord cutter and removable clamp of FIG. 1 shown in an open position without the blade.

To hold shells 12 and 14 in a partially open initial position as shown in FIGS. 4 and 5, cooperating guides 62 and 64 are provided on shells 12 and 14, respectively. Guides 62 and 64, which preferably have rounded or chamfered nibs 92 that allow initial engagement of guides 62 and 64 and that cause guides 62 and 64 to bear against one another as shells 12 and 14 are closed during the cutting process, serve as a detent to prevent shells 12 and 14 from opening up excessively so that cutter 10 may be easily handled in order to properly position an umbilical cord therein. Such an initial position is also a preferred starting position from which to begin the cutting process. A cutout 65 is provided in shells 12 and 14 to accommodate guides 62 and 64 when shells 12 and 14 are closed.

Figure 6:
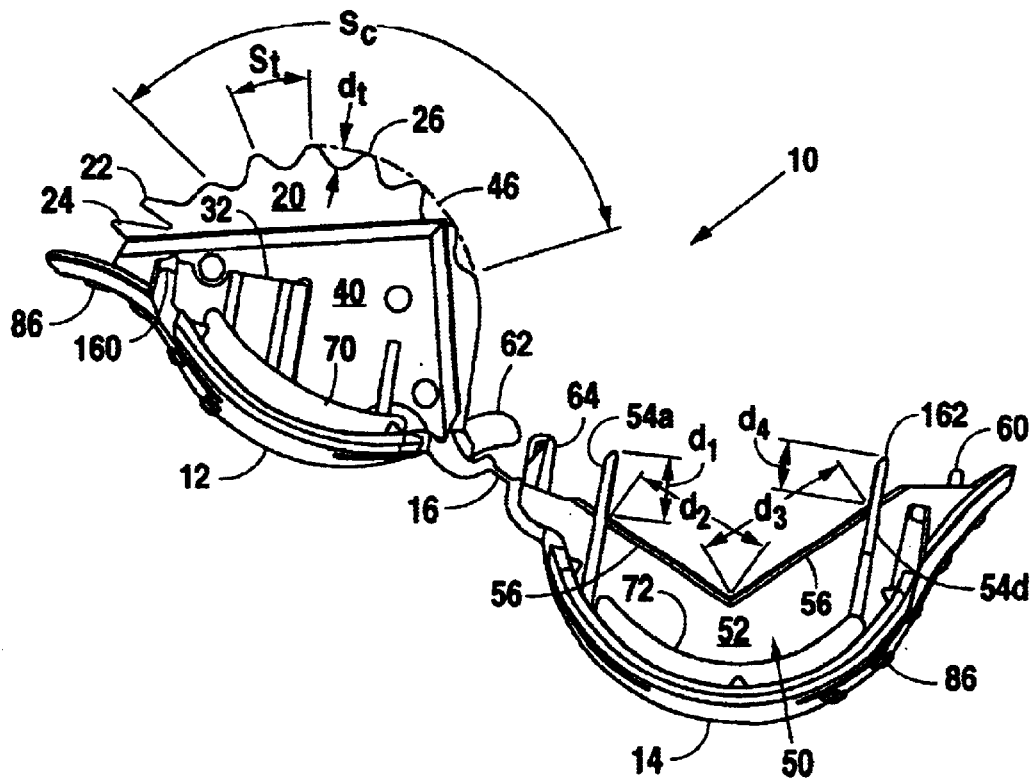
FIG. 6 is a front elevational view of the umbilical cord cutter of FIG. 1 shown in an open position.
Figure 7:
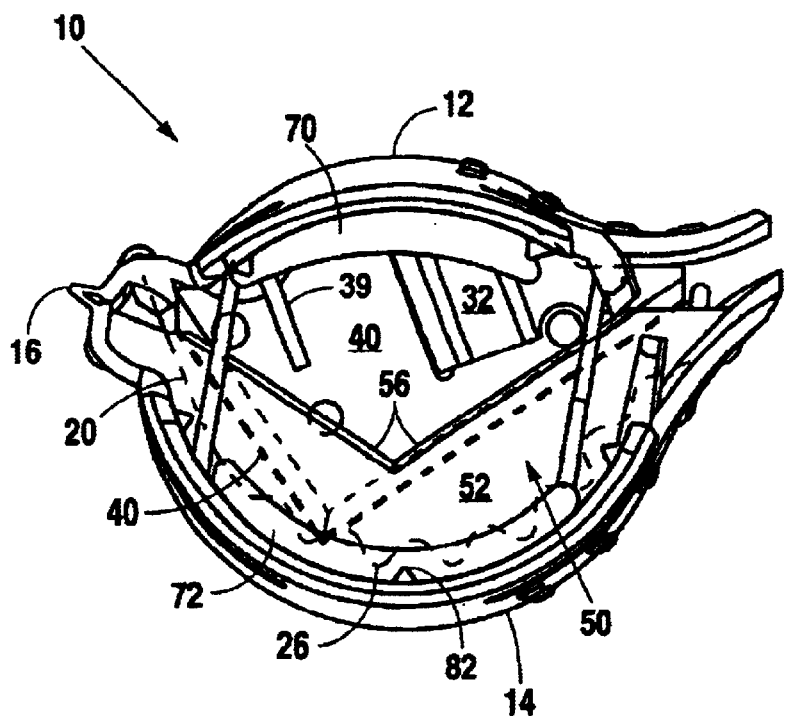
FIG. 7 is a front elevational view of the umbilical cord cutter of FIG. 1 shown in a closed position.

FIGS. 6 and 7 illustrate the relationship of blade 40 to clamping member 20 and cutting support 50 in open and closed cutter positions, respectively. As shown in FIG. 6, blade 40 (including the pointed tip of blade 40) is shallower than imaginary arc 46 of clamping member 20 at all points such that clamping member 20 will begin to engage the umbilical cord before blade 40 does so as cutter 10 is closed. Additionally, the recession of blade 40 below clamping member 20 helps to prevent medical personnel from being cut while handling cutter 10. Although cutter 10 may be made in any suitable size, in order to accommodate umbilical cords ranging from about 5 to 20 mm in diameter, the radius of arc 46 is preferably about 0.62 in., the distance $S_c$ along arc 46 is preferably about 1.3 in., the depth $d_t$ of teeth 26 is preferably about 0.08 in., the distance $S_t$ between successive teeth 26 along arc 46 is preferably about 0.22 in., the combined total of distances $d_1$, $d_2$, $d_3$, and $d_4$ is preferably about 1.6 in., and the thickness $T_c$ of clamping member 20 (best shown in FIG. 11) is preferably about 0.05 in. If $T_c$ is too thin, clamping member 20 would tend to cut the umbilical cord rather than pinch it as desired; if $T_c$ is too thick, clamping member 20 would tend to crush the umbilical cord. Almost immediately after clamping member 20 begins to engage the umbilical cord, the blood flow within the umbilical cord begins to decrease as the umbilical cord is constricted and cut. This physiological phenomenon helps to reduce the amount of blood that is available to squirt out of the umbilical cord during the cutting process. The blood that does squirt out of the umbilical cord during the cutting process is trapped by shells 12 and 14, which prevents splattering of blood and thereby improves cleanliness of the operating room and reduces the risk of blood born diseases to persons in the operating room. As shown in FIG. 7, blade 40 protrudes all the way past edges 56 of walls 52 of cutting support 50 to accomplish a clean, complete severance of the umbilical cord. Because blade 40 is shallower than clamping member 20 and clamping surface 108, and because edges 56 of cutting support 50 are elevated above the interior surfaces of shell 14 and strap 104 with which clamping member 20 and clamping surface 108 respectively cooperate to compress the umbilical cord on either side of blade 40, clamping member 20 and clamping surface 108 place the umbilical cord in tension across cutting support 50, which further enhances the cutting performance of blade 40 by pulling the cord apart at the cut.

Figure 8:
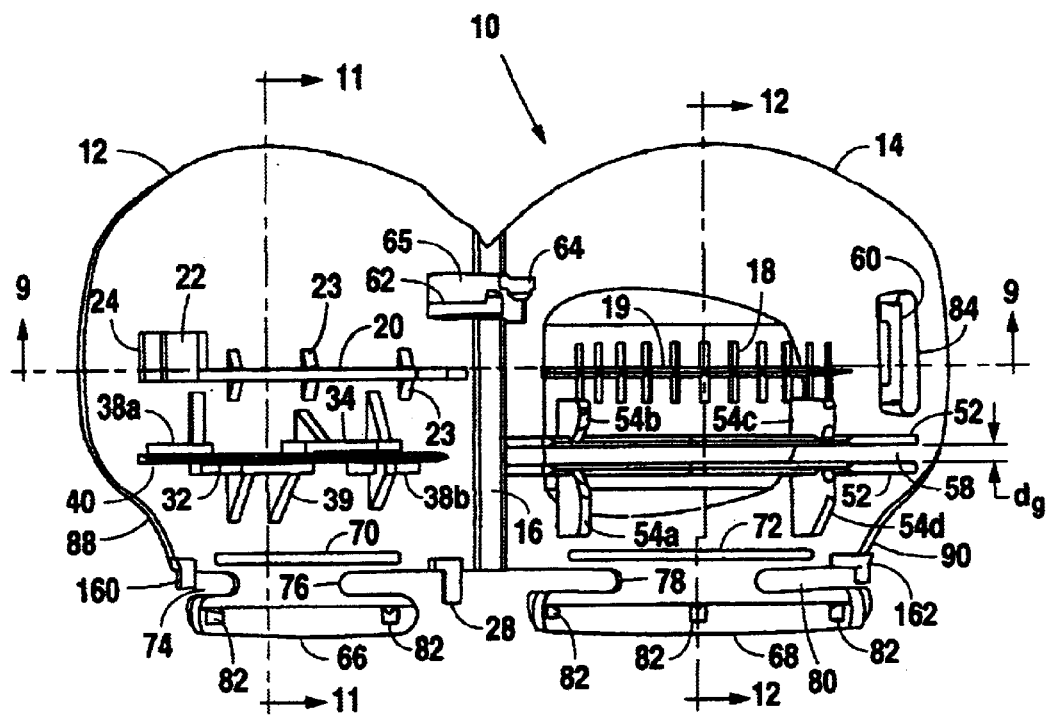
FIG. 8 is a top view of the umbilical cord cutter of FIG. 1 shown in an open position.
Figure 9:
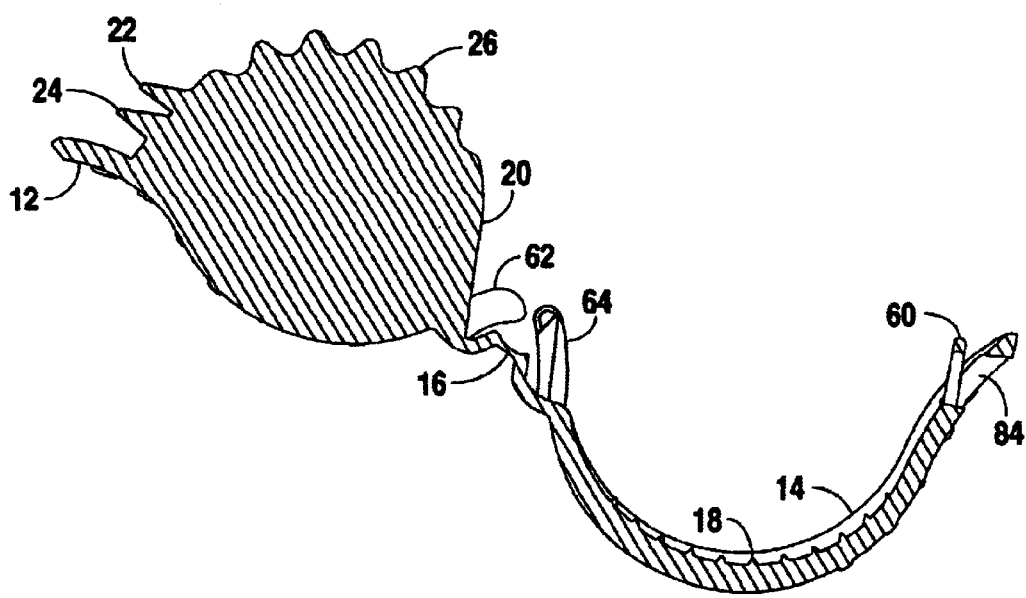
FIG. 9 is a sectional view taken along line 9—9 of FIG. 8.
Figure 10:
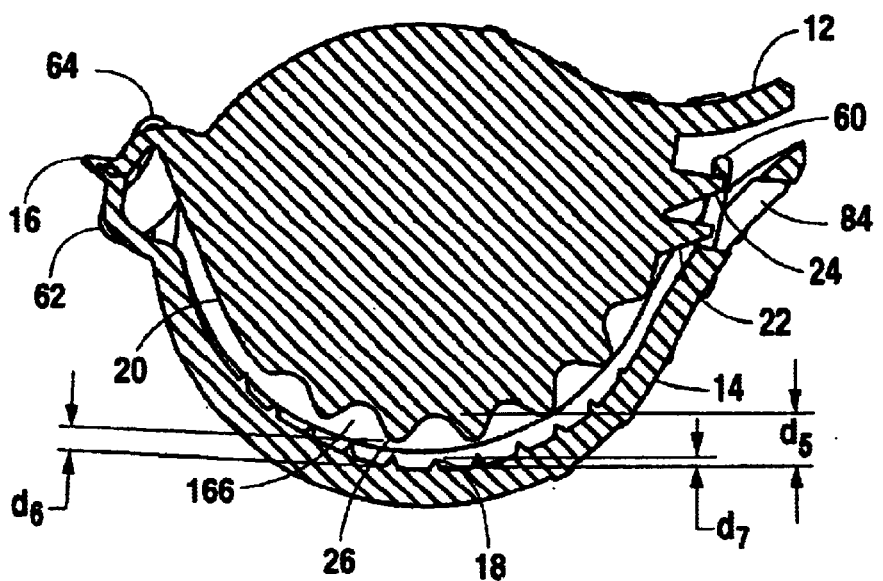
FIG. 10 is a sectional view similar to FIG. 9 but with the umbilical cord cutter in a closed position.

FIGS. 8–10 illustrate the relationship of clamping member 20 to ridges 18 and 19 and also the relationship of tabs 22 and 24 to catch 60 and opening 84. As shown in FIG. 8, clamping member 20 is longitudinally aligned with ridge 19, which is centered on ridges 18. FIGS. 9 and 10 show the lateral cross-section of cutter 10 through clamping member 20, ridges 18, and catch 60 with cutter 10 in an open and closed position, respectively. As shown in FIG. 10, in the closed position, tab 24 is engaged with catch 60 to prevent shells 12 and 14 from opening inadvertently, and clamping member 20 is brought to a position in which a small gap 166 exists between clamping member 20 and shell 14. The umbilical cord (not shown) is compressed within gap 166 and is held firmly in place by teeth 26 and ridges 18. Gap 166 is sized such that the umbilical cord is compressed sufficiently so as to completely shut off the flow of blood within the umbilical cord. Preferably, to accommodate umbilical cords ranging from about 5 to 20 mm in diameter, gap 166 is sized such that the distance $d_5$ (from the roots of teeth 26 to the interior surface of shell 14) is about 0.15 in., the distance $d_6$ (from the tips of teeth 26 to the interior surface of shell 14) is about 0.07 in., and the distance $d_7$ (from the interior surface of shell 14 to the tips of ridges 18) is about 0.03 in.

Figure 11:
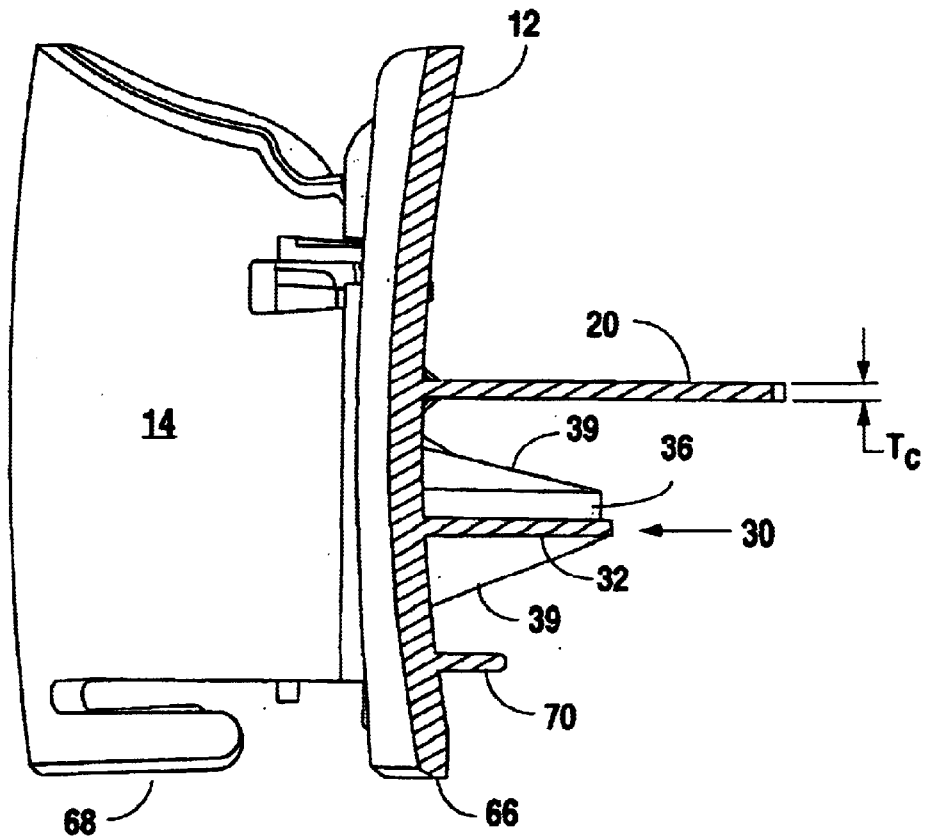
FIG. 11 is a sectional view taken along line 11—11 of FIG. 8.
Figure 12:
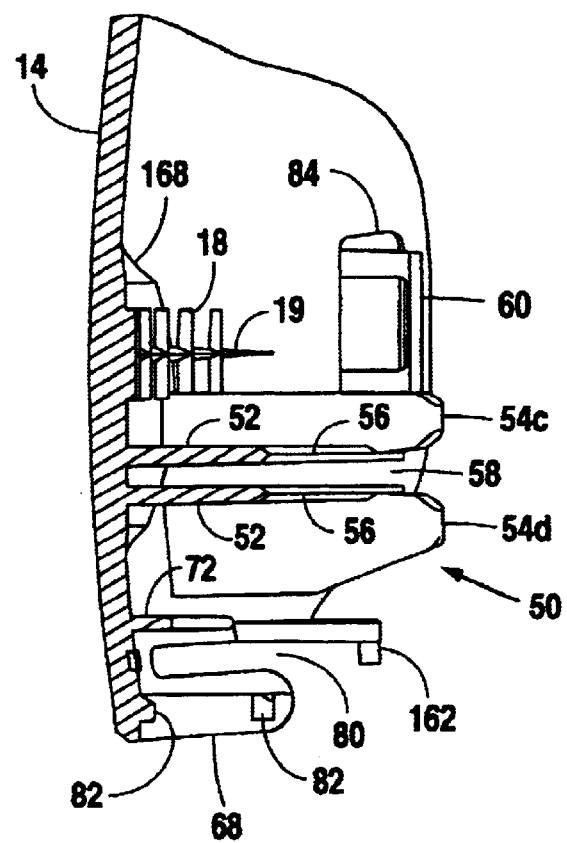
FIG. 12 is a sectional view taken along line 12—12 of FIG. 8.
Figure 13:
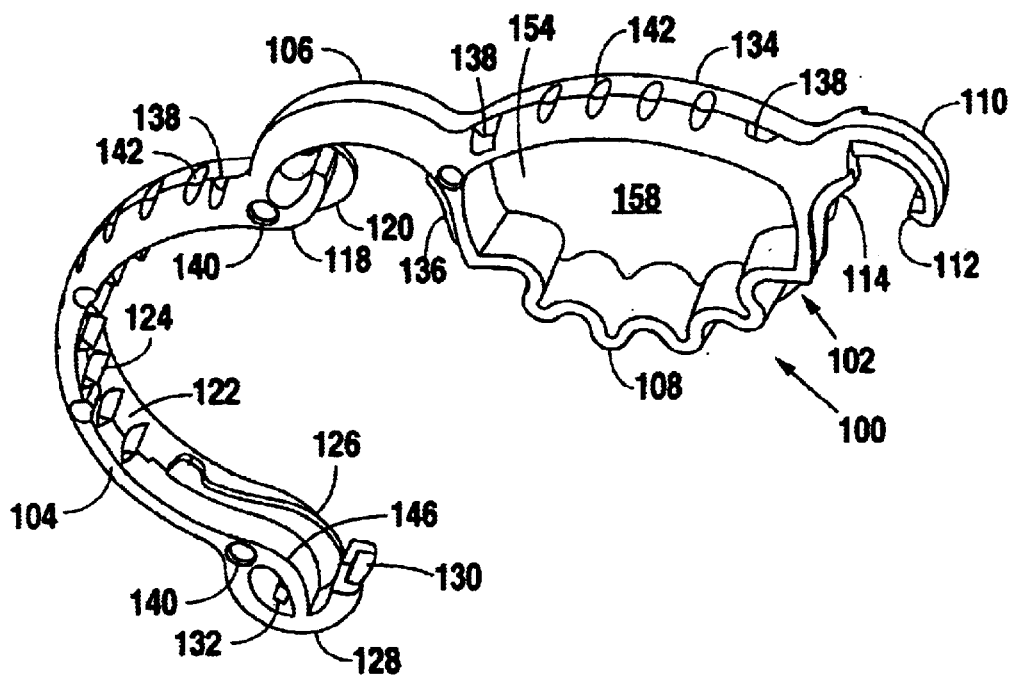
FIG. 13 is a perspective view of the removable clamp of FIG. 1 shown in an open position.

FIG. 11 shows a longitudinal cross-section of shell 12 passing through clamping member 20, blade holder 30, and fence 70. As seen in FIG. 11, shell 12 preferably has a slight longitudinal curvature as well as lateral curvature for ease in handling. Similarly, FIG. 12 shows a longitudinal cross-section of shell 14 passing through ridges 18, 19, walls 52 of cutting support 50, fence 72, and nub 82. Shell 14 preferably has a thickened area 168 in the vicinity of ridges 18, 19 and walls 52 of cutting support 50 to eliminate the longitudinal curvature on the interior of shell 14 at ridges 18, 19 so that ridges 18, 19 better cooperate with clamping member 20 and to increase the strength and stiffness of cutting support 50. Like shell 12, shell 14 preferably has a slight longitudinal curvature as well as lateral curvature for ease in handling.

Figure 20:
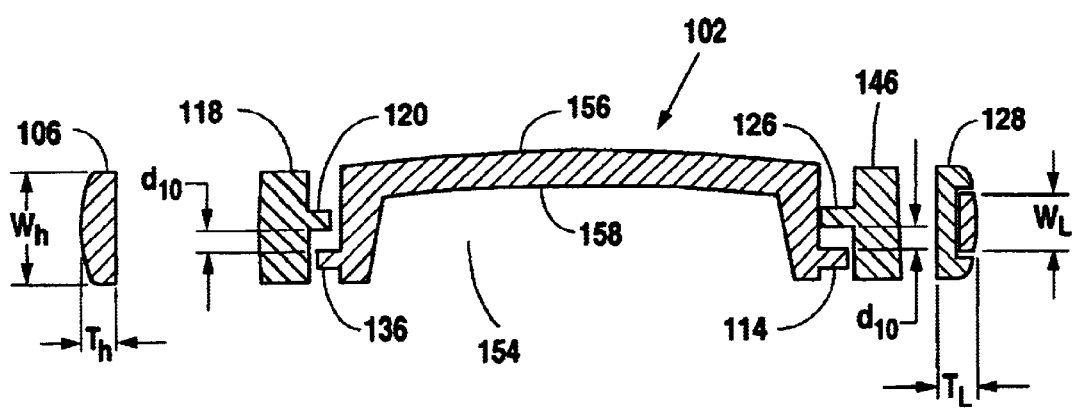
FIG. 20 is a sectional view taken along line 20—20 of FIG. 15.

As shown in FIGS. 13–17, baby clamp 100 comprises a clamp body 102 and a strap 104 connected by a hinge 106. Clamp body 102 preferably has a corrugated clamping surface 108 for clamping the umbilical cord in cooperation with the inner surface 122 of strap 104, which preferably has a plurality of ridges 124 to help grip the umbilical cord. To save weight, clamp body 102 preferably has a central cavity 154 bounded by clamping surface 108 and a crown 134. When baby clamp 100 is installed in cutter 10, back surface 158 faces away from cutter 10 (as best shown in FIG. 1) and face 156 faces toward the interior of cutter 10 (as best shown in FIG. 4). At the end of strap 104 opposite hinge 106, strap 104 has an ear 128 with a slot 130 for receiving a hook 110 that depends from clamp body 102 opposite hinge 106. Hook 110 has a catch 112 that cooperates with a recess 132 (best seen in FIGS. 4 and 5) for holding baby clamp 100 in the closed position. The thickness of hook 110 preferably varies from about 0.06 in. at dimension $d_8$ to about 0.04 in. at dimension $d_9$, and the width $W_L$ of hook 110 (best shown in FIG. 20) is preferably about 0.13 in. Hook 110 preferably subtends an angle $\theta_L$ of about 117 degrees with an inner arc length of about 0.31 in. As shown in FIG. 20, the overall thickness $T_L$ of ear 128 and hook 110 is preferably about 0.09 in. Hinge 106 preferably has an arc length $S_H$ of about 0.68 in. Crown 134 and strap 104 preferably have a plurality of recesses 138 for cooperating with nubs 82 on shelves 66, 68 to hold baby clamp 100 in cutter 10. Ridges 114 and 136, which depend from clamp body 102, cooperate with ridges 120 and 126 of strap 104 to close the gap between clamp body 102 and strap 104 in the vicinity of hinge 106 and ear 128 when baby clamp 100 is closed. A curved closeout 118 is preferably provided on the end of strap 104 adjacent hinge 106 to help prevent the umbilical cord from slipping into hinge 106. For symmetry, a similar closeout 146 may be provided on ear 128. When baby clamp 100 is closed, the umbilical cord will lie compressed in the gap 174 between strap 104 and clamp body 102 and will be held firmly in place by clamping surface 108 and ridges 124. To accommodate umbilical cords ranging from about 5 to 20 mm in diameter, radius $R_s$ of strap 104 is preferably about 0.56 in., and distance $S_s$ between ridges 120 and 126 along the interior surface 122 of strap 104 is preferably about 1.08 in. Tooling holes 140 may be provided to help remove baby clamp 100 from its mold during manufacturing. The exterior surfaces of crown 134 and strap 104 preferably have a plurality of recesses 142 to help the user grip baby clamp 100. As is readily apparent from the drawings, when baby clamp 100 is closed, a preferred shape of baby clamp 100 resembles the head of a koala bear. Accordingly, face 156 of clamp body 102 may be provided with protrusions that form a pair of eyes 148, a nose 150, and a mouth 152. Cavity 154 may also be utilized to house a sensor (not shown) for tracking the location of the baby after baby clamp 100 has been installed.

Preferably, cutter 10 and baby clamp 100 are each molded as a single piece of material. Alternatively, cutter 10 and baby clamp 100 may be machined or manufactured according to other methods known in the art. Although a variety of materials may be used, the preferred material is polycarbonate, which may be translucent and may be manufactured in a variety of colors. Because cutter 10 is intended to be a disposable product, hinge 16 need not be capable of many openings and closings of shells 12 and 14. The present inventors have found that hinge 16 is preferably about 0.02 in. thick if polycarbonate material is used. In describing the best mode of practicing this invention, a number of dimensions are disclosed herein for various features of the invention. However, it should be recognized that such dimensions, like polycarbonate material, are simply preferred, and this invention is not limited to the dimensions or materials described herein.

Figure 17:
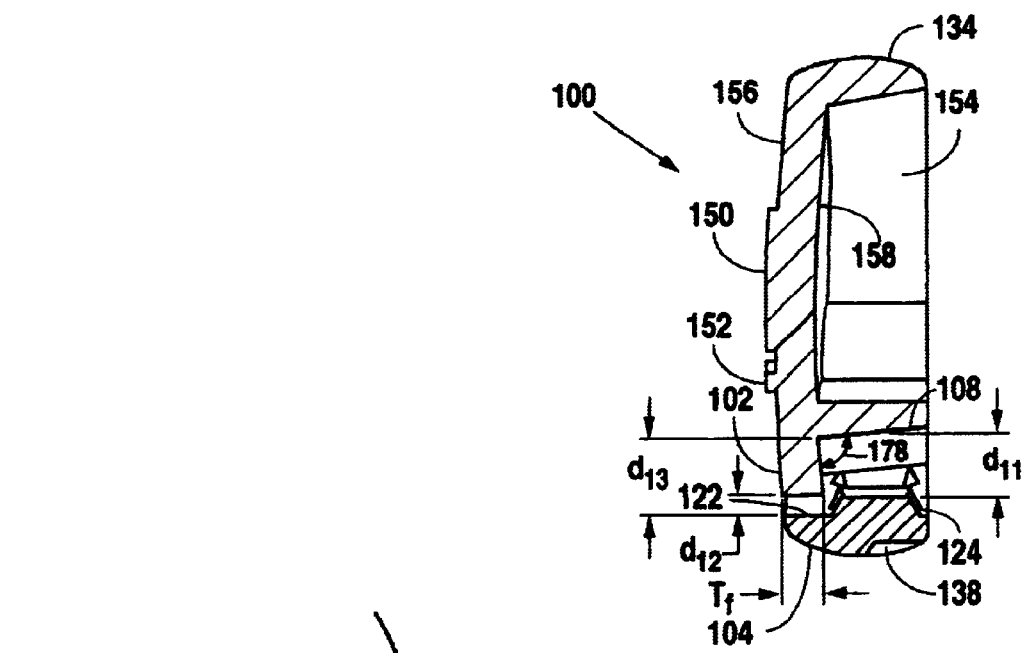
FIG. 17 is a sectional view taken along line 17—17 of FIG. 16.
Figure 19:
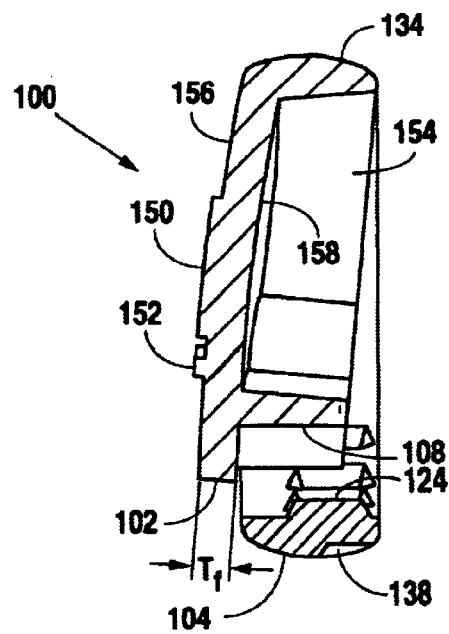
FIG. 19 is a sectional view similar to FIG. 17 showing displacement of the face of the removable clamp.

In order to accommodate umbilical cords ranging from about 5 to 20 mm in diameter, baby clamp 100 is designed such that clamp body 102 moves toward the interior of cutter 10 during the clamping process. In that regard, the angle 178 between clamping surface 108 and clamp body 102 is preferably slightly more than 90 degrees. This obtuse angle 178 also helps in removing baby clamp 100 from the mold during manufacturing. Similar to teeth 26 on clamping member 20, the corrugations of clamping surface 108 also assist in accommodating cords of varying size. As an umbilical cord is being clamped, the upward pressure on clamping surface 108 causes torsional displacement of hinge 106 such that the lower edge of clamp body 102 moves away from strap 104 as shown in FIG. 19. This design of baby clamp 100 is such that, after the umbilical cord has been cut and baby clamp 100 is left on the infant's navel, pulling of baby clamp 100 in a direction away from the infant generally serves to tighten the grip of baby clamp 100 on the stub of the cord, which helps to prevent inadvertent removal of baby clamp 100 from the infant. As illustrated in FIG. 20, gaps having a distance $d_{10}$ of preferably about 0.05 in. are provided between ridges 120 and 136 and ridges 126 and 114 to allow clamp body 102 to move as hinge 106 flexes. For proper flexure, hinge 106 preferably has a thickness $T_h$ of about 0.06 in. and a width $W_h$ of about 0.25 in. As shown in FIGS. 17 and 19, the lower edge of clamp body 102 preferably has a thickness $T_f$ of about 0.08 in. to properly pinch the umbilical cord. As with clamping member 20 discussed above, if $T_f$ is too thin, clamp body 102 would tend to cut the umbilical cord rather than pinch it as desired; if $T_f$ is too thick, clamp body 102 would tend to crush the umbilical cord.

FIGS. 17, 22, 23, and 24 illustrate preferred distances between strap 104 and clamp body 102 when baby clamp 100 is in the closed position in order to snugly clamp umbilical cords ranging from about 5 to 20 mm in diameter. Specifically, distances $d_{11}$ through $d_{22}$ preferably have the following approximate dimensions:

$d_{11} \approx 0.08$ in.;
$d_{12} \approx 0.06$ in.;
$d_{13} \approx 0.11$ in.;
$d_{14} \approx 0.04$ in.;
$d_{15} \approx 0.06$ in.;
$d_{16} \approx 0.07$ in.;
$d_{17} \approx 0.12$ in.;
$d_{18} \approx 0.05$ in.;
$d_{19} \approx 0.15$ in.;
$d_{20} \approx 0.03$ in.;
$d_{21} \approx 0.04$ in.;
$d_{22} \approx 0.06$ in.

Distances $d_{11}$, $d_{14}$, $d_{17}$, $d_{20}$ are average distances from ridges 124 to clamping surface 108 in view of the slight inclination of clamping surface 108 at angle 178 as discussed above.

Figure 18:
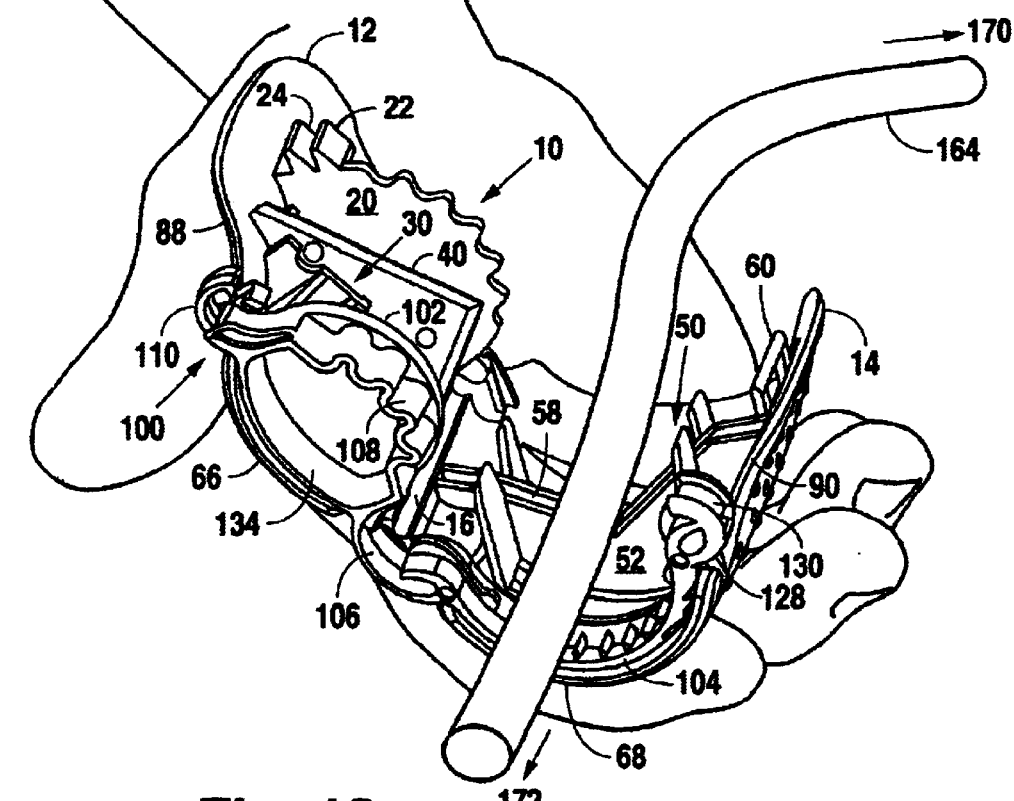
FIG. 18 is a perspective view illustrating the use of the umbilical cord cutter and removable clamp of FIG. 1.

The use of cutter 10 and baby clamp 100 in cutting an umbilical cord 164 is illustrated in FIG. 18. Umbilical cord 164 is placed in shell 14 so that umbilical cord 164 is generally centered in the "V" of walls 52 on cutting support 50. Cutter 10 and baby clamp 100 are oriented such that arrow 170 is toward the mother and arrow 172 is toward the baby. Once the umbilical cord 164 is thus placed, shell 12 is rotated about hinge 16 toward shell 14, and shelf 66 of shell 12 thereby rotates body 102 of baby clamp 100 about hinge 106 toward strap 104, which is supported by shelf 68 of shell 14. As shell 12 approaches shell 14, clamping member 20 engages cord 164 on the mother side of blade 40, and clamping surface 108 engages cord 164 on the baby side of blade 40. As the closing of cutter 10 and baby clamp 100 upon cord 164 continues, clamping member 20 and ridges 18, 19 (best shown in FIG. 3) firmly clasp cord 164 on the mother side of blade 40, and clamping surface 108 and ridges 124 firmly clasp cord 164 on the baby side of blade 40, which puts cord 164 in tension across cutting support 50. In the same closing motion, blade 40 severs cord 164 as blade 40 is forced into gap 58 between walls 52 of cutting support 50. The cutting performance is enhanced by the tension in cord 164, as discussed above. At the end of the closing motion, tabs 22 and 24 successively click into engagement with catch 60 to indicate that the cut is complete. After completion of the cut, the user removes baby clamp 100 from cutter 10 by placing his or her thumb 176 in the gap behind ear 128 formed by indentations 88 and 90 and forcing baby clamp 100 out of engagement with shelves 66, 68. The baby is then left with an aesthetically pleasing koala bear on its navel. Thus, the clamping and cutting of the umbilical cord 164 and the separation of the baby clamp 100 from the cutter 10 are easily accomplished with one hand of the user. Preferably, cutter 10 and baby clamp 100 are placed as close as possible to the baby before the cutting process is begun so that baby clamp 100 will be essentially adjacent the baby's tummy after the process is completed. Cutter 10 remains clamped to cord 164, which preserves the blood within cord 164 to be sent to the laboratory with the placenta (not shown) for any testing that may be necessary. Ultimately, cutter 10 is discarded along with cord 164 and the placenta.

The preferred embodiment shown in the drawings is designed primarily for right-handed use. It will be apparent to those skilled in the art that cutter 10 and removable baby clamp 100 may be made in the mirror image of that shown in the accompanying drawings for left-handed use. However, the present inventors have found that the configuration shown in the drawings is generally preferred by both right-handed and left-handed users.

Figure 21:
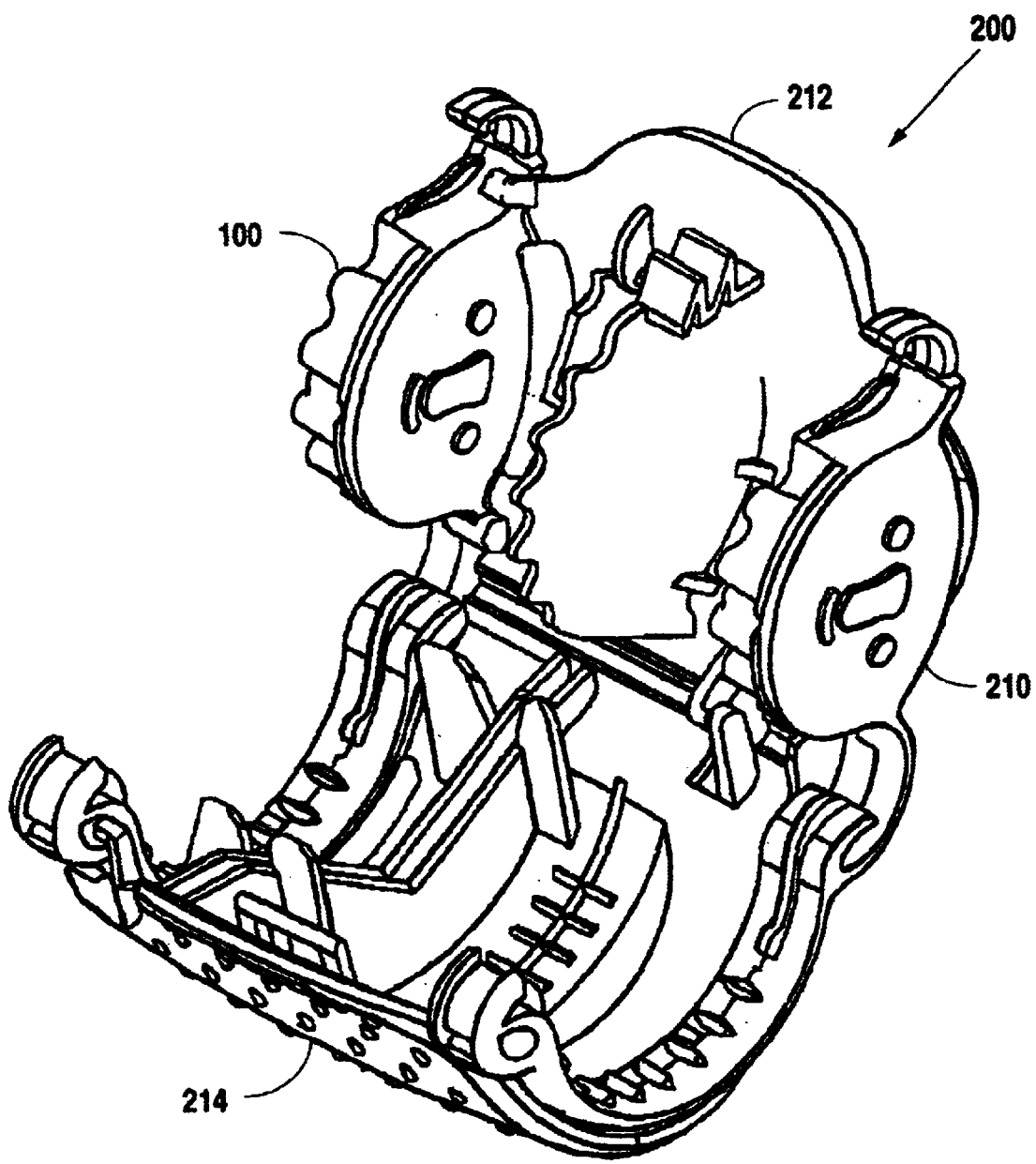
FIG. 21 is a perspective view of an alternative umbilical cord cutter with two removable clamps in accordance with the present invention shown in an open position.
Figure 22:
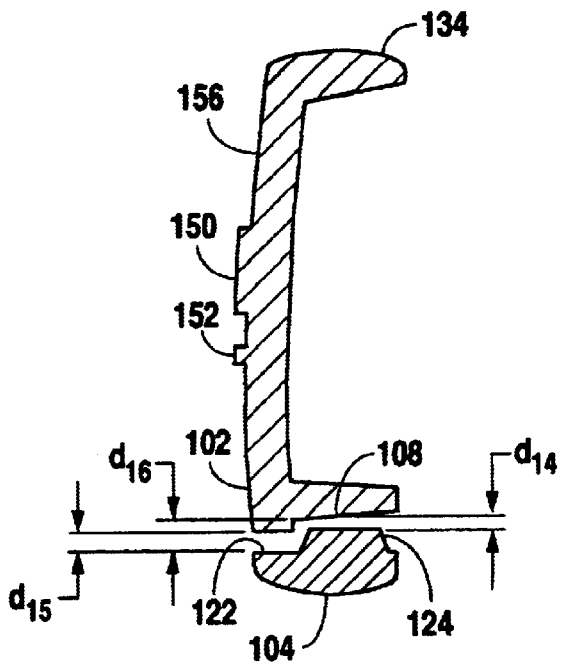
FIG. 22 is a sectional view taken along line 22—22 of FIG. 16.
Figure 23:
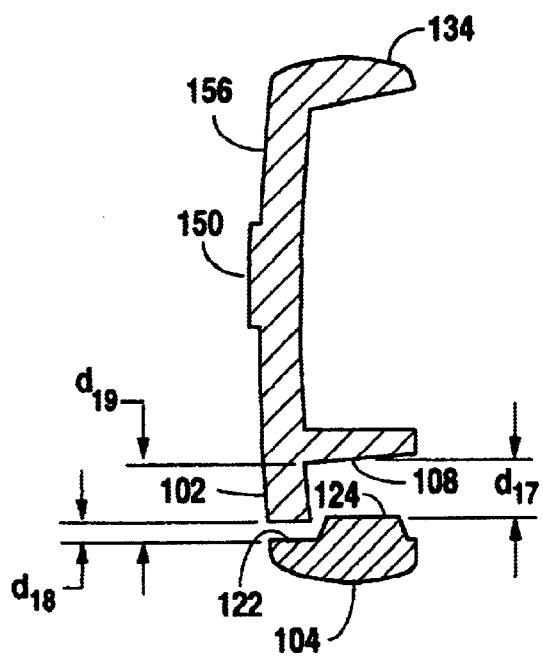
FIG. 23 is a sectional view taken along line 23—23 of FIG. 16.
Figure 24:
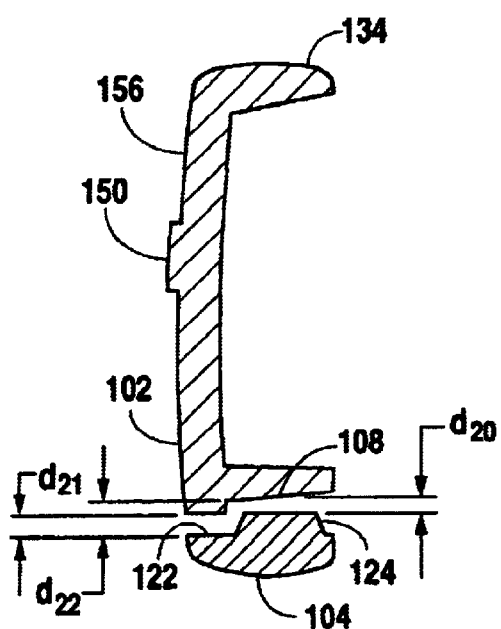
FIG. 24 is a sectional view taken along line 24—24 of FIG. 16.

Preferably, cutter 10 and baby clamp 100 are provided pre-assembled in the open position within a sterile package. Although the primary use of baby clamp 100 is in conjunction with cutter 10 as described above, baby clamp 100 may also be used to clamp an umbilical cord separate from cutter 10. Additionally, as shown in FIG. 21, the present invention may comprise a cutter 200 with two removable clamps 100 and 210, one on each end of shells 212 and 214. After cutter 200 has been used to sever the umbilical cord, both clamps 100 and 210 may be removed from cutter 200; clamp 100 remains with the infant, and clamp 210 remains with the cord and placenta.

Figure 25:
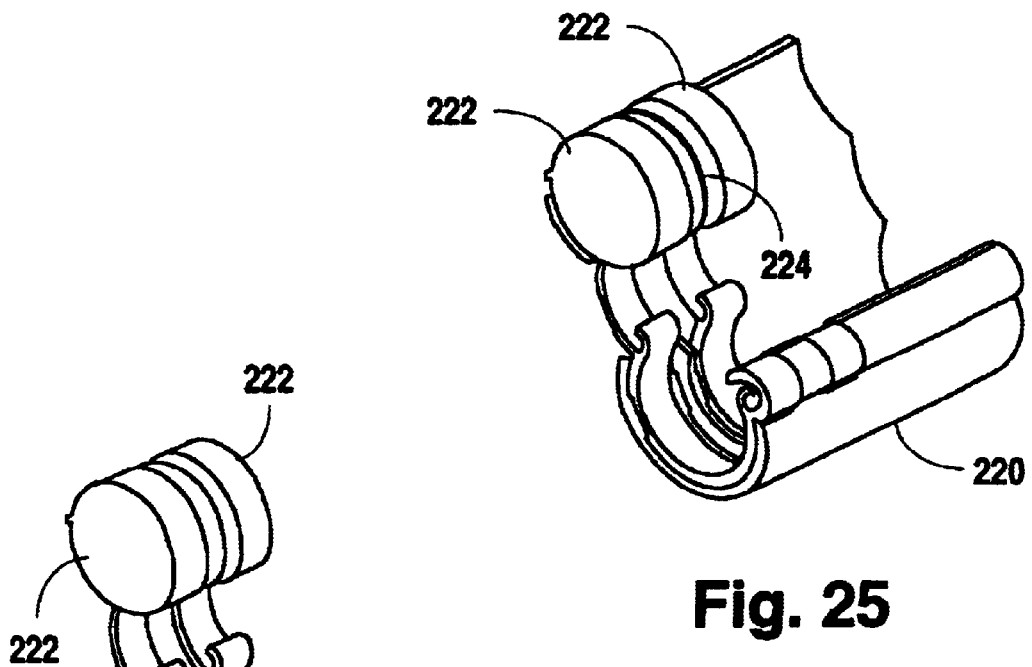
FIG. 25 is a perspective view of another alternative umbilical cord cutter and clamp in accordance with the present invention.
Figure 26:
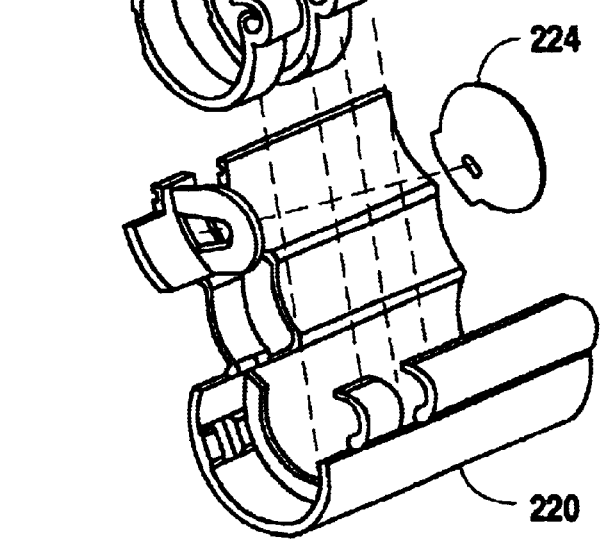
FIG. 26 is an exploded perspective view of the umbilical cord cutter and clamp of FIG. 25.
Figure 27:
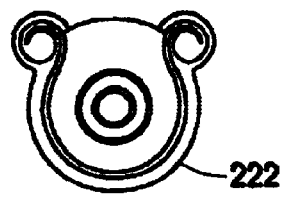
FIG. 27 is a front elevational view of the clamp of FIG. 25.
Figure 28:
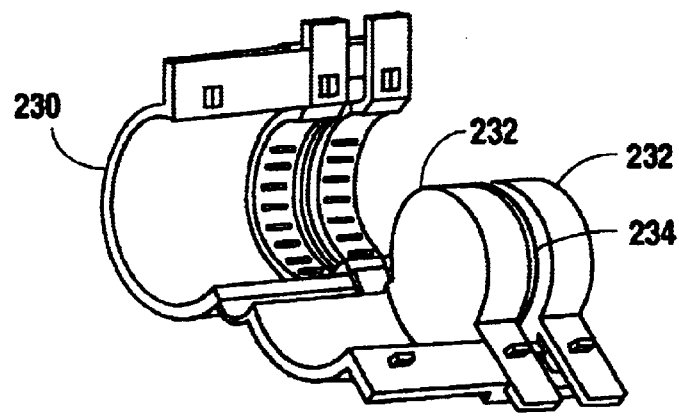
FIG. 28 is a perspective view of yet another alternative umbilical cord cutter and clamp in accordance with the present invention.
Figure 29:
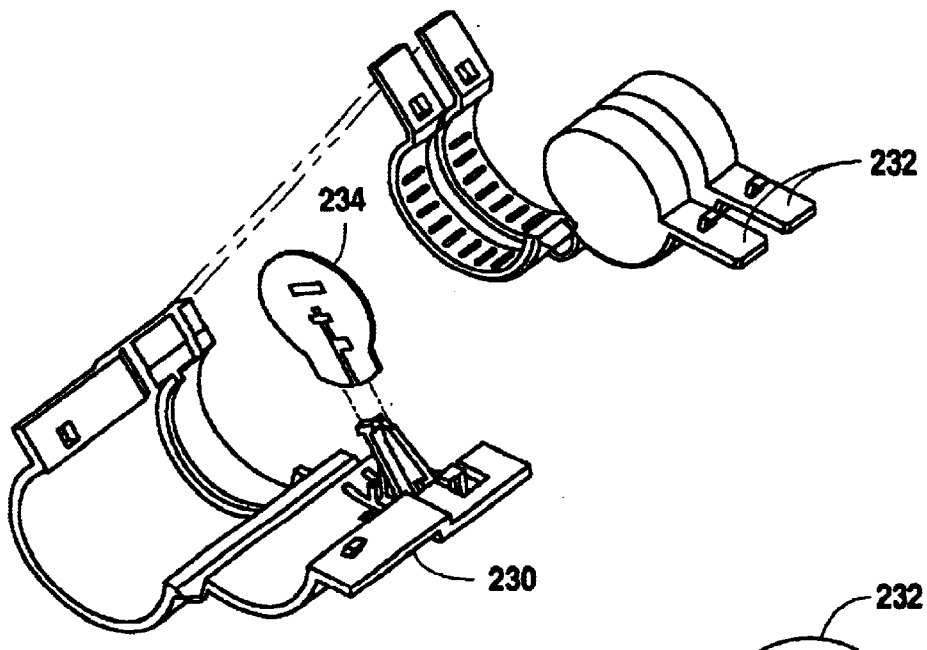
FIG. 29 is an exploded perspective view of the umbilical cord cutter and clamp of FIG. 28.
Figure 30:
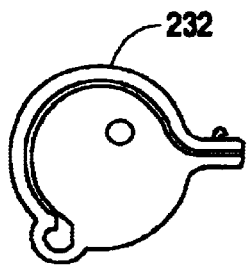
FIG. 30 is a front elevational view of the clamp of FIG. 28.

The removable clamp of this invention may also be made in the likeness of animals other than koala bears and in other non-animal shapes. For example, FIGS. 25–27 illustrate an umbilical cord cutter 220 in accordance with this invention having a circular blade 224 and a pair of removable clamps 222 in the shape of a teddy bear head. Similarly, FIGS. 28–30 illustrate an umbilical cord cutter 230 in accordance with this invention having a circular blade 234 and a pair of removable clamps 232 in the shape of a duck head, and FIGS. 31–35 illustrate an umbilical cord cutter 240 in accordance with this invention having an elliptical blade 244 and a removable clamp 242 in the shape of an ellipse that may be made to resemble a mouse (FIG. 33), a cat (FIG. 34), or an owl (FIG. 35). Thus, although the preferred shape is that of a koala bear, the removable clamp of this invention may take on many other shapes.

Although the foregoing specific details describe a preferred embodiment of this invention, persons reasonably skilled in the art will recognize that various changes may be made in the details of this invention without departing from the spirit and scope of the invention as defined in the appended claims. Therefore, it should be understood that this invention is not to be limited to the specific details shown and described herein.

We claim:

1. A device for clamping and cutting an umbilical cord, said device comprising:
   a first shell;
   a second shell movably connected to said first shell;
   a blade depending from one of said first and second shells, and a cutting support depending from the other of said first and second shells for supporting the umbilical cord;
   a clamping depending from one of said first and second shells; and
   a baby clamp engageable with and removable from said first and second shells;
   wherein by closing movement of said first and second shells, said clamping member and said baby clamp respectively compress the umbilical cord and said blade severs the umbilical cord between said clamping member and said baby clamp;
   wherein said baby clamp comprises a clamp body having an arcuate clamping surface, an arcuate strap, a hinge connecting said clamp body to said strap, and a latch for holding said clamp body and said strap in a closed position with the umbilical cord compressed between said clamping surface and said strap.

2. The device of claim 1, wherein said clamp body comprises a face surface that faces in a first direction and wherein said clamp body, said strap, and said hinge cooperate with the umbilical cord in said closed position such that pulling on said baby clamp in said first direction tightens said baby clamp onto the umbilical cord.

3. A device for clamping and cutting an umbilical cord, said device comprising:
   a first shell and a second shell, said first shell having a first means for clamping the umbilical cord in cooperation with said second shell at a first location along the umbilical cord, said second shell having a means for supporting the umbilical cord;
   a second means for clamping the umbilical cord at a second location spaced apart from said first location along the umbilical cord, said second means for clamping being engageable with and removable from said first and second shells;
   a means for movably connecting said first and second shells; and
   a means for cutting the umbilical cord between said first and second locations;
   wherein said second means for clamping comprises a clamp body having an arcuate clamping surface, an arcuate strap, a binge connecting said clamp body to said strap, and a latch for holding said clamp body and said strap in a closed position with the umbilical cord compressed between said clamping surface and said strap.

4. The device of claim 3 wherein said clamp body comprises a face surface that faces in a first direction and wherein said clamp body, said strap, and said hinge cooperate with the umbilical cord in said closed position such that pulling on said second means for clamping in said first direction tightens said second means for clamping onto the umbilical cord.

5. A device for clamping an umbilical cord, said device comprising:
   a clamp body having an arcuate clamping surface;
   an arcuate strap movably connected to said clamp body; and
   a latch for fastening said strap to said clamp body with the umbilical cord compressed between said clamping surface and said strap.

6. The device of claim 5 wherein said device resembles at least a portion of an animal.

7. The device of claim 6 wherein said device resembles the head of a koala bear.

8. The device of claim 6 wherein said device resembles the head of a teddy bear.

9. The device of claim 6 wherein said device resembles the head of a duck.

10. The device of claim 6 wherein said device resembles a mouse.

11. The device of claim 6 wherein said device resembles a cat.

12. The device of claim 6 wherein said device resembles an owl.

13. The device of claim 5 wherein said strap is hingedly connected to said clamp body.

14. The device of claim 5 wherein said clamping surface comprises a plurality of corrugations.

15. The device of claim 5 wherein said clamp body, said strap, and said latch comprise a single integral structure.

16. The device of claim 15 wherein said single integral structure comprises a polycarbonate material.

* * * * *

UNITED STATES PATENT AND TRADEMARK OFFICE
CERTIFICATE OF CORRECTION

PATENT NO.     : 6,740,095 B2
DATED          : May 25, 2004
INVENTOR(S)    : Richard L. Watson Jr. et al.

It is certified that error appears in the above-identified patent and that said Letters Patent is hereby corrected as shown below:

<u>Title page,</u>
Item [75], Inventors, please change "Philip Y.C. Leung" to -- Philip C.Y. Leung" --.

<u>Column 5,</u>
Line 18, insert a period -- . -- after "shell 12";
Lines 38 and 39, replace "dg" with -- $d_g$ --.

<u>Column 11,</u>
Line 16, insert the word -- member -- after the word "clamping";

<u>Column 12,</u>
Line 7, replace "binge" with -- hinge --.

Signed and Sealed this

Tenth Day of August, 2004

JON W. DUDAS
*Acting Director of the United States Patent and Trademark Office*